United States Patent [19]
Marnett et al.

[11] Patent Number: 5,475,021
[45] Date of Patent: Dec. 12, 1995

[54] COMPOUNDS AND COMPOSITIONS FOR INHIBITION OF CYCLOOXYGENASE ACTIVITY

[75] Inventors: Lawrence J. Marnett, Brentwood; Amit S. Kalgutkar, Nashville, both of Tenn.

[73] Assignee: Vanderbilt University, Nashville, Tenn.

[21] Appl. No.: 162,404

[22] Filed: Dec. 3, 1993

[51] Int. Cl.$^6$ ................ C07D 207/325; C07D 207/452; A61K 31/40
[52] U.S. Cl. .................... 514/425; 548/545; 548/547; 548/548; 548/549
[58] Field of Search ............... 514/425; 548/545, 548/547, 548, 549

[56] References Cited

U.S. PATENT DOCUMENTS

| | | | |
|---|---|---|---|
| 3,337,583 | 8/1967 | Knock | 548/547 X |
| 4,851,547 | 7/1989 | Kita et al. | 548/548 |
| 4,970,139 | 11/1990 | Bagchi | 430/449 |
| 5,124,347 | 6/1992 | Connor et al. | 514/418 |

FOREIGN PATENT DOCUMENTS

| | | | |
|---|---|---|---|
| 4-308567 | 10/1992 | Japan | 548/547 |
| 1533067 | 11/1978 | United Kingdom | |

OTHER PUBLICATIONS

Pal, I., Odenwaller, R. and Marnett, L. J. "7–Oxabicycloheptylprostanoic Acids: Potent, Time–Dependent Cyclooxygenase Inhibitors That Induce a Conformational Change in the Prostaglandin Synthase Protein". *J. Med. Chem.* 1992, 35, 2340–2342.

Schoneich, C., Dillinger U., Bruchhausen, F., and Asmus, K. "Oxidation of Polyunsaturated Fatty Acids and Lipids through Thiyl and Sulfonyl Radicals: Reaction Kinetics, and Influence of Oxygen and Structure of Thiyl Radicals" *Archives of Biochemistry and Biophysics*, 1992, vol. 292, No. 2, 456–467.

Higgs, G. A., Salmon, J. A., Henderson, B., and Vance, J. R. "Pharmacokinetics of aspirin and salicylate in relation to inhibition arachidonate cyclooxygenase and antiinflammatory activity" *Proc. Natl. Acad. Sci.* USA 1986, vol. 84, 1417–1420.

Humber, L. G. (1987) "Etodolac: The Chemistry, Pharmacology, Metabolic Disposition, and Clinical Profile of a Novel Anti–Inflammatory Pyranocarboxylic Acid" *Medicinal Research Reviews*, vol. 7, No. 1, 1–28.

Wells, I. and Marnett, L. J. "Acetylation of Prostaglandin Endoperoxide Synthase by N–Acetylimidazole: Comparison to Acetylation by Aspirin" *Biochemistry*, 1992, vol. 31, No. 40, 9520–9525.

Wells, I. and Marnett, L. J. "Inactivation of Prostaglandin Synthase by Acylating Derivatives of Indomethacin" *Biochemistry*, 1993, 32, 2710–2716.

Meade, E. A., Smith, W. L., and DeWitt, D. L. "Differential Inhibition of Prostaglandin Endoperoxide Synthase (Cyclooxygenase) Isozymes by Aspirin and Other Non–steroidal Anti–inflammatory Drugs" *The Journal of Biological Chemistry*, 1993, vol. 268, No. 9, Issue of Mar. 25, 6610–6614.

Smith, W. L., DeWitt, D. L., Shimokawa, T., Kraemer, S. A., and Meade, E. A. "Molecular Basis for Inhibition of Prostanoid Biosynthesis by Nonsteroidal Anti–inflammatory Agents", 1990, vol. 21, No. 12, IV 24–IV 28.

Rome, L. H. and Lands, W. E. M. "Structural requirements for time–dependent inhibition of prostaglandin biosynthesis by anti–inflammatory drugs" *Proc. Natl. Acad. Sci*, USA, 1975, vol. 72, No. 12, 4863–4865.

Walsh, D. A., Young, S., Shamblee, D. A., Welstead, W., Jr., Nolan, J. C., and Graff, G. "Nonsteroidal Antiiflammatory Drug Hydroxamic Acids. Dual Inhibitors of Both Cyclooxygenase and 5–Lipoxygenase" *J. Med. Chem.* 1990, 33, 2070–2072.

Smith, W. L. and Marnett, L. J. "Prostaglandin Endoperoxide Synthase: Structure and Catalysis." *Biochimica et Biophysica Acta*, 1991, 1083, 1–17.

*Primary Examiner*—Jacqueline Haley
*Attorney, Agent, or Firm*—Waddey & Patterson; Arles A. Taylor, Jr.

[57] ABSTRACT

The present invention includes N-substituted maleimides (1(H)-Pyrrole-2,5-dione (Maleimide) analogs and succinimides which act as potent nonsteroidal anti-inflammatory drugs and are capable of dual inactivation or selective inactivation of the cyclooxygenase and the peroxidase activities of prostaglandin endoperoxide synthase (PGHS).

44 Claims, 7 Drawing Sheets

1: R = H
2: R = CH$_3$

15: R = (CH$_2$)$_7$CH$_3$
16: R = (CH$_2$)$_8$CH$_3$
17: R = (CH$_2$)$_9$CH$_3$

18: n = 7
19: n = 8
20: n = 9

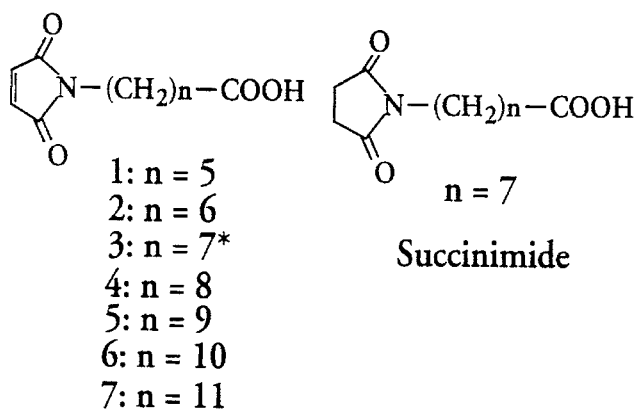

1: n = 5
2: n = 6
3: n = 7*
4: n = 8
5: n = 9
6: n = 10
7: n = 11

Succinimide n = 7

*The irreversible inactivation by maleimide analog 3 was proved when the corresponding succinimide derivative was synthesized and did not inactivate the enzyme.

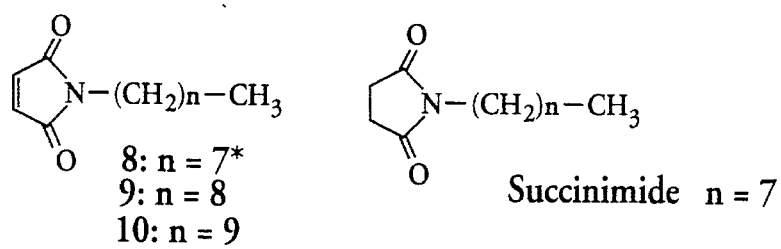

8: n = 7*
9: n = 8
10: n = 9

Succinimide n = 7

*Time dependent inactivation proved when corresponding succinimide derivative was not an time-dependent inactivator.

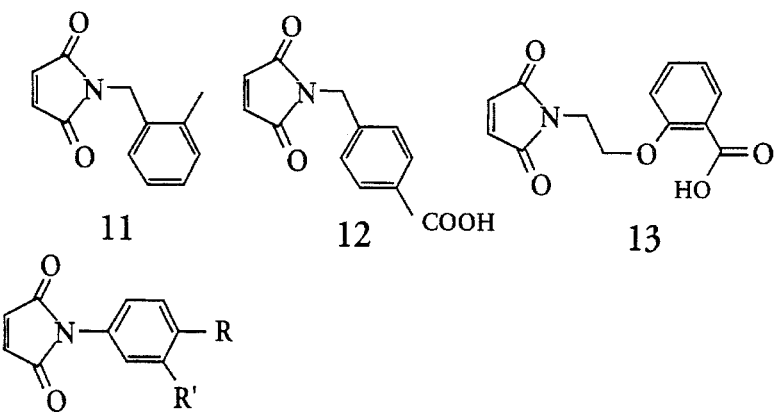

14: R = COOH; R' = OCOCH₃
15: R = OCOCH₃; R' = COOH

FIG. 7

COMPOUNDS AND COMPOSITIONS FOR INHIBITION OF CYCLOOXYGENASE ACTIVITY

This invention was made with government support under grant number CA 47479 from the National Institutes of Health (NIH). The United States government has certain rights in the invention.

BACKGROUND OF THE INVENTION

The present invention relates generally to anti-inflammatory drugs and more particularly to novel compounds for inhibition of the cyclooxygenase activity of prostaglandin synthase, an essential enzyme in the prostaglandin synthesis pathway. Prostaglandins (PGs), leukotrienes (LTs), histamine, bradykinin, platelet-activating factor (PAF) and interleukin-1 have been implicated in inflammation reactions in tissues (Vane and Botting, 1987). With the exception of nonnucleated erythrocytes, all cells are capable of synthesizing PGs from arachidonic acid (as diagramed schematically in FIG. 1 by Smith, et at., 1991). PGs are released in response to many kinds of trauma or any disturbance of the cell membrane. The pathological release of PGs contributes to inflammation, fever and pain.

It will be appreciated by those skilled in the art that development of nonsteroidal anti-inflammatory drugs has focused primarily on inhibitors of cyclooxygenase activity of prostaglandin endoperoxide synthase. To this end, there have been numerous attempts to synthesize inhibitors of PGH synthase. Some well-known inhibitors are aspirin and other aspirin-like NSAIDs, including aryl acetic acids (among them indomethacin and its analogs), Etodolac (Humber, 1987) and anthranilic acids. The anti-inflammatory action of aspirin depends on the inhibition of $PGE_2$ synthesis by salicylate (Higgs, et at, 1987).

The mechanism of inactivation of cyclooxygenase activity of PGHS by the non-steroidal anti-inflammatory drug aspirin is well known (Vane, 1971). Aspirin inactivates the cyclooxygenase activity of holo PGHS by regioselective acylation of Ser 530 in sheep (Ser 529 in humans), which then blocks the entry of AA into the substrate binding site. Site-directed mutation of Ser 530 to Ala 530 maintains normal enzymatic activity suggesting that Ser 530 is not responsible for cyclooxygenase catalysis (Dewitt et at., 1990). It was thought that Ser 530 possessed the most reactive OH group in PGHS owing to an heme induced conformational change that placed electron rich residues with Ser 530, however subsequent studies with other acetylating agents such as N-acetylimidazole did not result in regioselective acetylation (Wells et al., 1992; Wells et al., 1993). These results suggested the importance of the carboxylic acid moiety in aspirin which could hydrogen bind in the vicinity of Ser 530 leading to covalent modification of Ser 530.

Attempts to construct a working model for the active site of fatty acid cyclooxygenase with the pattern recognition of known inhibitors as well as conformational minimizations of the natural substrate AA have been made. The Squibb group recently described a novel series of 7-oxabicycloheptylprostanoic acid derivatives that inhibit AA-induced platelet aggregation and AA oxygenation by platelet and bovine seminal microsomes (Pal, et at., 1992).

There are two isozymes of PGHS (PGHS-1 and PGHS-2) which share about 62% sequence identity with each other. They catalyze the first committed step of prostaglandin synthesis: the conversion of arachidonate to prostaglandin $H_2$ ($PGH_2$). A recent study indicates that these two isozymes are differentially sensitive to inhibition by common NSAIDs (Meade et at., 1993).

Among the attempts to invent effective nonsteroidal anti-inflammatory drugs are the disclosures for a wide variety of NSAIDs. U.S. Pat. No. 5,234,937 reveals 3,5-di-tertiary-butyl-4-hydroxyphenyl oxazolyl methanones and related compounds which act as antiinflammatory agents. The related U.S. Pat. No. 5,234,939 covers 3,5-tertiary-butyl-4-hydroxyphenyl imidasolyl methanones and related compounds which function as antiinflammatory agents. A series of U.S. Pat. Nos. 4,981,865, 5,075,330, and 5,112,846 by Belliotti et al protect N-hydroxyamide, N-hydroxythioamide, hydroxyurea, and N-hydroxythiourea derivatives of selected NSAIDs which act as antiinflammatory agents. Numerous other patents protect a wide variety of NSAIDs. The scientific literature reveals a plethora of NSAIDs, also. NSAIDs can be characterized into five groups:

(1) the propionic acid derivatives;

(2) the acetic acid derivatives;

(3) the fenamic acid derivatives;

(4) the biphenylcarboxylic acid derivatives; and (5) the oxicams or a pharmaceutically acceptable salt thereof. However, of these NSAIDs in use today, only aspirin is known to bind covalently with its target enzyme which results in an irreversible interaction. In contrast, the majority of NSAIDs bind competitively with their target enzymes giving rise to a reversible interaction between the NSAID and its target enzyme.

What is needed, then, is a compound which acts as a potent NSAID and covalently binds to the active site on the PGHS enzyme. This compound is presently lacking in the prior art.

SUMMARY OF THE INVENTION

The present invention is a compound of the formula

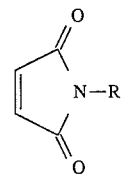

isomers thereof, or a pharmaceutically acceptable salt thereof, wherein R is a moiety selected from the group consisting of an alkyl of 1–11 carbon atoms; an alkyl of 1–11 carbon atoms when substituted by alkyl, carboxyl alkyl and carboxyl, phenoxy, or carboxyl substituted phenoxy; phenyl; phenyl when substituted by alkyl, carbonyloxy, or carboxyl and acetyl; benzyl; and benzyl when substituted by alkyl, carboxyl, or carbonyloxy.

The present invention is also a compound of the formula

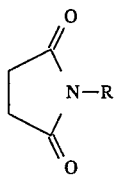

isomers thereof, or a pharmaceutically acceptable salt thereof; wherein R is a moiety selected from the group consisting of an alkyl of 1–11 carbon atoms; an alkyl of 1–11 carbon atoms when substituted by alkyl, carboxyl, alkyl and carboxyl, phenoxy, or carboxyl substituted phenoxy; phenyl; phenyl when substituted by alkyl, carbonyloxy, or carboxyl and acetyl; benzyl; and benzyl when substituted by alkyl, carboxyl, or carbonyloxy.

The present invention is also a pharmaceutical composition for the treatment of conditions advantageously effected by the inhibition of one or both peroxidase and cyclooxygenase activities of PGHS which comprises an amount effective for the treatment of the condition of the compound of Formula I or Formula II defined above or the pharmaceutically acceptable salt thereof together with a pharmaceutically acceptable carrier. Compounds of this invention are inhibitors of the synthesis of the products of one or both of the enzymes cyclooxygenase and paroxidase of the PGHS enzyme and for the treatment of the conditions meant to include rheumatoid arthritis, osteoarthritis, other inflammatory conditions, psoriasis, pain, allergic diseases, asthma, inflammatory bowel disease, cardiovascular conditions including ischemic heart disease and artherosclerosis and ischemia-induced cell damage, particularly brain damage caused by stroke. Such conditions are exemplary in nature and are in no way meant to limit the scope of the invention. Thus, the present invention is also a method for treatment of the condition as noted above in a mammal, including humans, suffering therefrom.

The invention also provides for use of any such compound of Formula I or Formula II or salt thereof in the manufacture of a medical therapeutic agent.

The pharmaceutical composition of Formula I or Formula II or use of the compound or salt of Formula I or II is meant to include treatment understood to be prophylactic pertinent to the foregoing named conditions. The preferred compound of the present invention is a compound of the Formula I wherein the compound is N-8-(maleimido)octanoic acid.

BRIEF DESCRIPTION OF THE DRAWINGS

FIG. 7 is a set of drawings depicting structural formulas of numbered compounds discussed in Tables 1–5. Compound numbers correspond to the compound numbers listed in Tables 1–5 found in Example 3.

LIST OF TABLES

Figure 1:
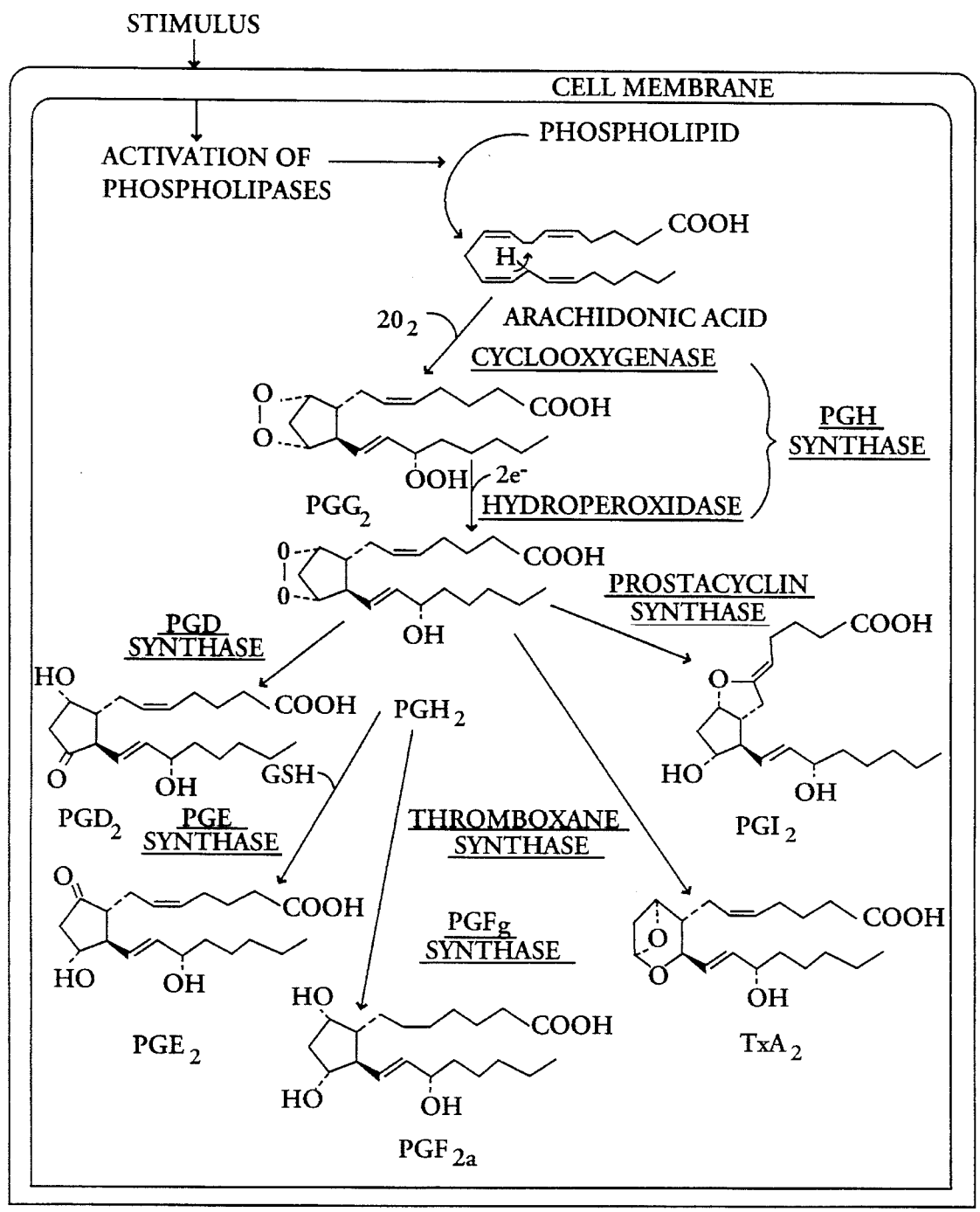
FIG. 1 is a schematic of the biosynthetic pathway for production of inflammatory and thrombotic mediators from arachidonic acid. The first step of the pathway is catalyzed by the cyclooxygenase activity of PGHS. The compounds of this invention inhibit this cyclooxygenase activity.

1 Instantaneous Inactivation of the Cyclooxygenase Activity of Holo Prostaglandin 2 IC50 Values for Inactivation of Cyclooxygenase Activity 3 Time Dependent Inactivation of Cyclooxygenase Activity by N-Maleimido-w-aminoacids 4 Studies Towards Instantaneous Inactivation of Peroxidase Activity by N-Maleimido-w-aminoacids 5 Time Dependent Inhibition of Peroxidase Activity by Compound

DESCRIPTION OF THE PREFERRED EMBODIMENT

Several 1(H)-Pyrrole-2,5-dione (Maleimide) analogs were synthesized and found to be potent time-dependent inactivators of both the cyclooxygenase and the peroxidase activities of ram seminal vesicle purified PGHS. The maleimide analogs containing a long chain alkyl group with a terminal carboxylic acid substituent displayed instantaneous inactivation of the cyclooxygenase activity of PGHS whereas the corresponding N-alkylmaleimides lacking the acid moiety failed to instantaneously inactivate the cyclooxygenase activity, although they displayed time- and concentration-dependent inactivation. Structure-activity studies indicate that the most potent instantaneous inactivation occurs when the distance between the maleimide ring and the terminal carboxylic acid moiety corresponds to seven methylenes. The corresponding saturated N-8-(succinimido)octanoic acid analog did not inactivate PGHS suggesting that the inactivation resulted in covalent modification. Higher concentrations of the N-(maleimido)alkanoic acids were required to inactivate the peroxidase activity of PGHS. These results aid in gaining additional insights on the inhibitor-protein association and would serve as attractive templates in the rational designing of cyclooxygenase inhibitors.

The cyclooxygenase activity of prostaglandin endoperoxide (PGH) synthase is responsible for the first mandatory step in the arachidonic acid cascade which involves the stereospecific oxygenation of arachidonic acid (AA) at the 13-pro-S center leading to the corresponding prostaglandin endoperoxide $PGG_2$. The peroxidase activity of PGHS then reduces the endoperoxide to the corresponding alcohol $PGH_2$. Heme is essential for both the cyclooxygenase and peroxidase activities. $PGH_2$ is then metabolized further to thromboxanes, prostacylin, and prostaglandins $E_2$ and $F_{2\alpha}$. Quite recently there has been considerable interest in the mechanism leading to the stereoselective oxygenation of arachidonic acid. Karthein et al. (1988) detected a transient protein-derived free radical upon addition of arachidonic acid or PGG$_2$ to PGHS which was identified as a tyrosyl radical. These studies led to the proposal that this protein-derived tyrosyl radical plays the critical role of the oxidant in the stereospecific hydrogen atom abstraction of AA. Similar conclusions were reached Kulmacz et al. (1990). Kinetic studies on the tyrosyl radical formation and decay could not be correlated to the time frame of arachidonic acid oxygenation by PGHS which had been reconstituted with fe(III) protoporphyrin IX or Mn(III) protoporphyrin IX. The Mangano enzyme is prepared by removal of the heme group normally found associated with PGHS and substitution of that group with a mangano protoporphyrin molecule. It has very low peroxidase activity and is not capable of generating tyrosyl radicals during incubations of AA with PGHS. These studies led to the conclusion that the tyrosyl radicals generated are not catalytically competent in the cyclooxygenase reaction and that their formation reflects oxidative inactivation of the enzyme.

Chemical model studies have demonstrated that thiyl free radicals generated from a variety of sources including glutathione, cysteine, N-acetylcysteine, and mercaptoethanol react with polyunsaturated fatty acids by hydrogen transfer and addition to double bonds and the corresponding absolute rate constants for H-abstraction were in excess of $10^7$ sec$^{-1}$. The reactivity of thiyl free radicals towards polyunsaturated fatty acids is known to be more pronounced because of lower C—H bond energies (lower pKa's) for the bisallylic methylene groups which generates pentadienyl radicals capable of adding oxygen as shown below.

maleimide and N-(7-dimethylamino-4-methylcoumarinyl) maleimide (DACM) which prevents the oxidation of AA. Results of these experiments suggest that NEM inactivates holo but not the apo PGHS wheras the reverse is true with DACM. Preliminary data from peptide mapping experiments suggests that NEM modifies mainly Cys 313, Cys 512 and Cys 540. Modification of apo PGHS by DACM results in the loss of heme binding. Site-directed mutagenesis experiments to mutate these cysteines to serines and their corresponding effect on prostaglandin biosynthesis are presently being carried out.

The chemical objective was two-fold. The first task was to design and synthesize much more potent maleimide analogs capable of inactivating PGHS rapidly at a much lower concentration than those previously employed for easier peptide mapping. Furthermore, pharmacological manipulation of the arachidonic acid cascade along both the cyclooxygenase and lipooxygenase pathways, continues to be an area of intense activity towards the designing of anti-inflammatory agents. The recent discovery of the isozyme of PGHS-1, PGHS-2 which shares about 62% sequence identity with PGHS-1 has opened new avenues of research in drug discovery. The observation that expression of PGHS-2 is stimulated by mediators of inflammation in immune cells and that glucocorticoids inhibit this process is suggestive of the fact that PGHS-2 may be responsible for the production of prostanoids involved in inflammation and/or mitogenesis. Therefore, we have designed selective inhibitors of PGHS-2, the sensitivity of which towards substrates and inhibitors is not yet known. The mechanism

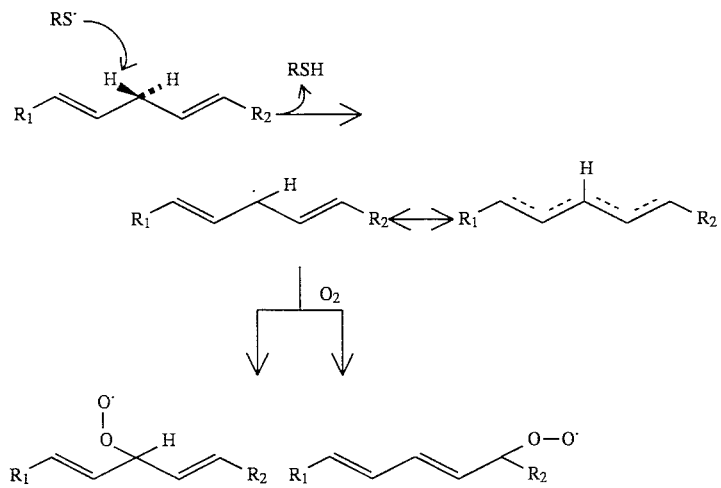

In accord with the proposal the rate constants for H-abstraction in the case of bisallylic methylene substrates exceeded those for H-abstraction from other substrates such as alcohol and ethers by at least three orders of magnitude. The fact that thiyl free radicals were able to promote the facile peroxidation of polyunsaturated fatty acids led to the possibility that thiyl radicals generated in higher biological systems such as enzymes may be responsible for lipid peroxidation.

Figure 2:
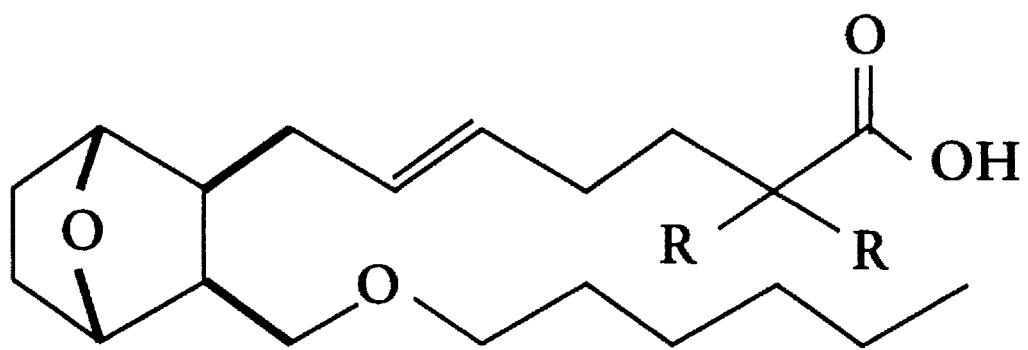
FIG. 2 is a structural drawing of arachidonic acid analogs described in the preferred embodiment. Compound numbers correspond to compound numbers in bold at pages 10–11 in the description of the preferred embodiment.

Thiyl radicals (as reviewed in Shoeneich, 1992) can be potentially generated from cysteines present in PGHS, in the catabolism of arachidonic acid. The problem has been studied from a chemical perspective resulting in the demonstration of time- and concentration-dependent inactivation of both the cyclooxygenase and the peroxidase activities of PGHS by two cysteine specific reagents, namely N-ethylof inactivation of PGHS by the non-steroidal anti-inflammatory drug aspirin was chosen as the basis of this research (FIG.2).

The most potent compound of the series is analog 1, which possesses bis-exo substitution of the oxabicycloheptane ring. In addition to inhibition of cyclooxygenase activity in vitro, analog 1 prevents AA-induced sudden death in the mouse and AA-induced changes in lung mechanics in guinea pigs at doses much below those required for similar effects by indomethacin. Analog 2 displays the same activities as analog 1, but has a longer duration of action in vivo.

Studies on analog 2 in the laboratory has shown that analog 2 is a potent time-dependent inhibitor of cyclooxygenase activity of PGHS. The IC$_{50}$ of analog 2 at an enzyme concentration of 140 nM, was 80 nM with complete inhibition at 150 nM. Mechanistic studies indicated that analog 2 induces a conformational change in the PGHS protein. Preliminary structure-activity studies on compounds with structural similarity indicate the position of oxygen on the omega side chain and the stereochemistry on the oxobicycloheptane ring as the governing factors in the inhibition.

The basis for the inhibitory activity of a given NSAID depends on the interaction of the NSAID with the active site of the enzyme it inhibits. A working model for the active site of fatty acid cyclooxygenase with the pattern recognition of known inhibitors as well as conformational minimizations of the natural substrate AA has been constructed. The Squibb group recently described a novel series of 7-oxabicycloheptylpro stanoic acid derivatives that inhibit AA-induced platelet aggregation and AA oxygenation by platelet and bovine seminal microsomes. The most potent compound of the series is analog 1, which possesses bis-exo substitution of the oxabicycloheptane ring. In addition to inhibition of cyclooxygenase activity in vitro, analog 1 prevents AA-induced sudden death in the mouse and AA-induced changes in lung mechanics in guinea pigs at doses much below those required for similar effects by indomethacin, a well-known NSAID. Analog 2 displays the same activities as analog 1 but has a longer duration of action in vivo. Studies on analog 2 in the laboratory has shown that analog 2 is a potent time-dependent inhibitor of cyclooxygenase activity of PGHS. The $IC_{50}$ of analog 2 at an enzyme concentration of 140 nM, was 80 nM with complete inhibition at 150 nM. Mechanistic studies indicated that analog 2 induces a conformational change in the PGHS protein. Preliminary structure-activity studies on compounds with structural similarity indicate the position of oxygen on the omega side chain and the stereochemistry on the oxobicycloheptane ring as the governing factors in the inhibition.

In order to illustrate the present invention, reference is made to the following examples which, however, are not intended to limit the invention in any respect.

General Chemical Procedure

Melting points are uncorrected. $^1$H NMR spectra were recorded (in the Department of Chemistry, Vanderbilt University) on a Bruker WP-360 or WP-200 instrument in $CDCl_3$ or DMSO-$d_6$ (unless otherwise noted). Chemical shifts are expressed in parts per million relative to internal tetramethylsilane. Proton multiplicities are expressed in terms of abbreviations (s=singlet, bs=broad singlet, d=doublet, dd=doublet of doublets, t=triplet, q=quartet and m=multiplet. Electron impact mass spectra (EI-MS) were recorded on a Delsi nermag R10-10 C instrument. Fast atom bombardment mass spectra (FAB-MS) were recorded on a VG70–250HF mass spectrometer. Unless stated otherwise, starting materials were obtained from Aldrich chemical company, Milwaukee, Wis. and Lancaster Synthesis Inc., Windham, N.H. and were used without further purification. Solvents were obtained from Fisher scientific Pittsburg, Pa. and were HPLC grade. Column chromatography was performed using silica gel (60–100 mesh) from Fisher. Thin layer chromatography (TLC) was performed on silica gel GF 254 (Analtech).

Figure 3:
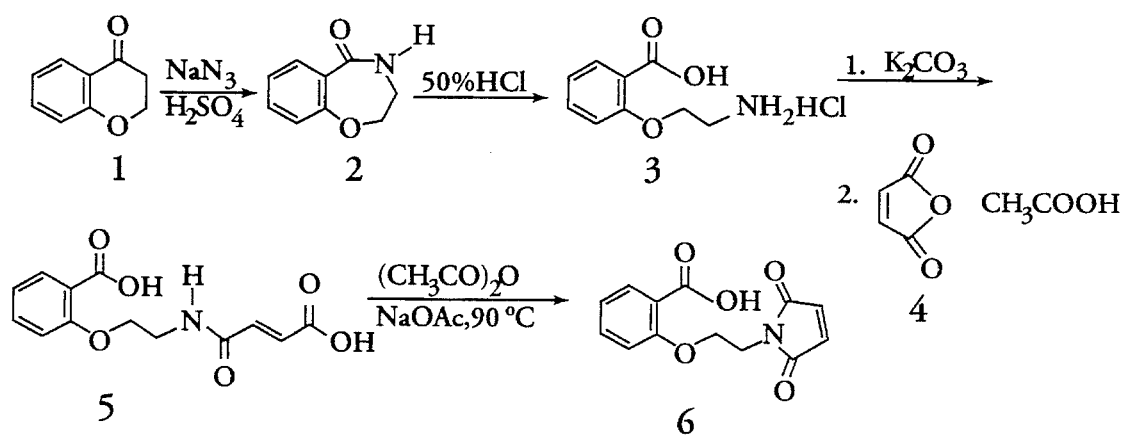
FIG. 3 is a schematic of synthesis of maleimides containing the aspirin moiety, specifically 2-[2-(N-Maleimidoethoxyl)]benzoic acid. Compound numbers correspond to compound numbers in bold in Example 1.
Figure 4:
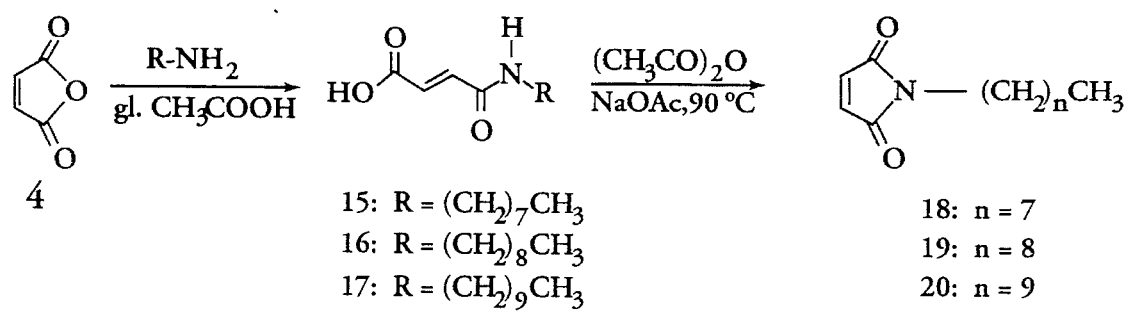
FIG. 4 is a schematic of general procedure for synthesis of N-substituted maleamic acids and N-substituted maleimides, as described in Example 2. Compound numbers correspond to compound numbers in bold in Example 2.
Figure 5:
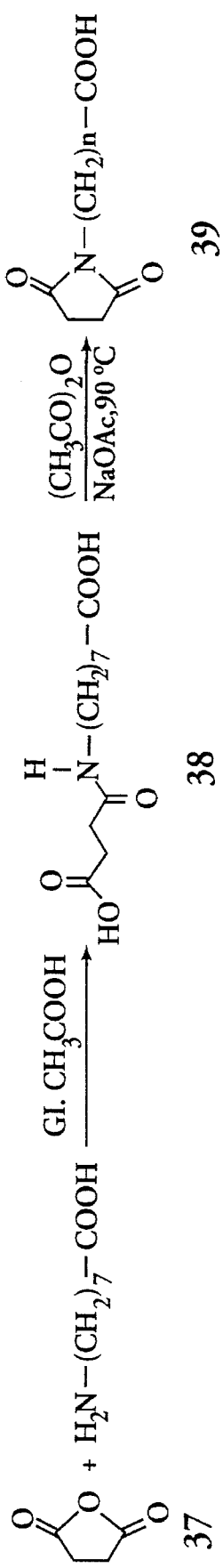
FIG. 5 is schematic of general procedure for synthesis of N-substituted succinamic acids and N-substituted succinimides, as described in Example 2.

The compound numbers in bold type refer to the compounds disclosed on FIGS. 3 and 4.

EXAMPLE 1

SYNTHESIS OF MALEIMIDES CONTAINING THE ASPIRIN MOIETY

Synthesis of 2-[2-(N-Maleimidoethoxy)]benzoic acid (FIG. 3)

First Step in the Synthesis of 2,3-Dihydro-1,4-benzoxazepin-5(4H)-one (2).

To a solution containing 4-chromanone (1, 2 g, 13.4 mmol) in 15 mL conc $H_2SO_4$ at 0° C. was added sodium azide (1.131 g, 17.4 mmol) and the reaction mixture was stirred initially at 0° C. for 1 hour and then stirred at room temperature for 2 hours. The reaction was quenched by the slow addition of water and then subsequently basified with 10% NaOH. The aqueous solution was extracted with ether (2×150 mL). The combined ether layers were dried ($Na_2SO_4$) and filtered. The solvent was removed under vacuo and the crude product was recrystallized from EtOAc/hexanes to afford 1.3 g, 61% of 2 as white needles. mp 118°–120° C. $^1$H NMR ($CDCl_3$) d 8.0 (d, 1 H ArH), 7.6–7.7 (bs, 1H, NH), 7.4 (t, 1H, ArH), 7.2 (t, 1H ArH), 7.0 (d, 1H, ArH), 4.4 (t, 2H, $CH_2$), 3.5 (t, 2H, $CH_2$). EIMS M$^+$ 163 (98), 134 (99), 105 (100).

Second Step in the Synthesis of Hydrochloride Salt of o-Aminoethoxybenzoic acid (3•HCl).

A reaction mixture containing: 2,3-dihydro-1,4-benzoxazepin-5(4H)-one (2, 2.5 g, 15.3 mmol) in 75 mL 6N HCl was heated in an oil bath at 110° C. for 24 hours. The reaction mixture was cooled and water (50 mL) was added and the aqueous solution was washed with ether (100 mL). The aqueous solution was evaporated under vacuo and the residue was recrystallized from EtOH/Ether to afford 2.89 g 87% of 3•HCl as a white crystalline solid. mp 182°–183° C.: $^1$H NMR (DMSO-$d_6$) d 11.9 (bs, 1H, COOH), 8.2–8.3 (bs, 2 H $N_2$), 7.6 (d, 1H, ArH), 7.5 (t, 1H, ArH), 7.2 (t, 1H, ArH), 7.0 (d, 1H, ArH), 4.3 (t, 2H, $CH_2$), 3.1 (t, 2H, $CH_2$). EIMS M$^+$ (-HCl) 182 (40), 164 (32), 133 (100).

Third Step in the Synthesis of Maleamic acid (5).

An aqueous solution of aminoethoxy benzoic acid hydrochloride (3•HCl, 720 mg, 3.3 mmol) in 10 mL of water (pH=1) was treated dropwise with aqueous potassium carbonate till a pH of 7 was obtained. The aqueous solution was evaporated under vacuo and the resultant white solid was stirred with maleic anhydride (4, 0.32 g, 3.3 mmol) in 10 mL of glacial acetic acid overnight. The resultant crystalline white solid which had seperated out of the reaction mixture was filtered and dried. The crude product was recrystallized from ethanol/water to afford 0.59 mg, 64% of white crystals. mp 161°–162° C. $^1$H NMR (DMSO-$d_6$) d 9.3 (bs, 1H, NH), 7.4–7.7 (m, 2 H, ArH), 7.0–7.3 (m, 2H, ArH), 6.4 (d, 1H, olefinic H), 6.2 (d, 1H, olefinic H), 4.2 (t, 2H, $CH_2$), 3.6 (t, 2H, $CH_2$). FABMS MH$^+$ 280 (70), 262 (60), 164 (98), 133 (100).

Final Step in the Synthesis of 2-[2-(N-Maleimidoethoxy)] benzoic acid (6).

A reaction mixture containing 5 (730 mg, 2.6 mmol) in 8 mL of acetic anhydride and sodium acetate (132 mg, 1.61 mmol) was heated in an oil bath at 90° C. for 2 hours. The reaction mixture was cooled and diluted with water. The aqueous solution was extracted with ether (2×30 mL). The combined organic solution was washed with brine (60 mL) and then with water. The organic solution was dried ($MgSO_4$), filtered and the solvent was evaporated to afford a yellow oil. The yellow oil was chromatographed on silica gel and eluted with EtOAc/Hexanes 1:1 to afford essentially pure 6 as a white solid (0.21 g, 31%). mp 145°–147° C. $^1$H NMR ($CDCl_3$) d 8.2 (d, 1H, $C_6$-H, ArH), 7.5–7.6 (t, 1 H, $C_5$-H, ArH), 7.2–7.3 (t, 1H, $C_4$-H, ArH), 7.0 (d, 1H, $C_2$-H, ArH), 6.7 (s, 2H, olefinic H), 4.4 (t, 2H, $CH_2$), 4.2 (t, 2H, $CH_2$). FABMS MH$^+$ 262 (26), 244 (84), 124 (99), 79 (100).

EXAMPLE 2

General Procedure for the Synthes of N-Substituted-maleamicacids and Succinamic acids.

A reaction mixture containing either maleic anhydride (4, 1 g, 10.19 mmol) or succinic anhydride (37, 1 g, 10 mmol) and the appropriate amine (10.19 mmol for 4 and 10 mmol for 37) in 20 mL of glacial acetic acid was stirred overnight. The solid which precipitated out of the reaction mixture was filtered, washed thoroughly with water and recrystallized from 2-propanol/water. In the case of the succinimide derivative, the corresponding succinamic acid did not precipitate out of the reaction mixture and hence the reaction mixture was concentrated and the residue was crystallized to afford the desired product (FIG. 4).

N-(o-Methylbenzyl)maleamic acid (7).

White solid from isopropanol/water. mp=163°–165° C., 78%. $^1$H NMR (DMSO-$d_6$) d 10.1 (s, 1H, COOH), 9.4 (s, 1H, NH), 7.3–7.4 (m, 4H, ArH), 6.6 (d, 1H, olefinic H), 6.4 (d, 1H, olefinic H), 4.5 (d, 2H, $C_6H_5CH_2$), 2.4 (s, 3H, ARCH$_3$). EIMS M$^+$ 219 (20), 201 (25), 120 (100), 104 (65).

N-(4-Carbonyloxybenzyl)maleamic acid (8).

White solid from isopropanol/water. mp=213°–216° C., 70%. $^1$H NMR (DMSO-$d_6$) d 9.4 (t, 1H, NH), 7.9 (d, 2H, ArH), 7.4 (d, 2H, ArH), 6.5 (d, 1H, olefinic H), 6.3 (d, 1H, olefinic H), 4.4 (d, 2H, benzylic CH$_2$).

N-4-Salicylmaleamic acid (11).

Dark yellow needles from Methanol/H$_2$O, mp=219°–220° C., 50%. $^1$H NMR (DMSO-$d_6$)d 11.4 (bs, 1H, COOH), 10.5 (s, 1H, NH), 7.6 (d, 1H, C-6 ArH), 7.4 (d, 1H, C-5 ArH), 7.15 (dd, 1H, C-3 ArH), 6.4 (d, 1H, olefinic H), 6.3 (d, 1H, olefinic H). EIMS M-18 233 (10), 215 (25), 153 (75), 135, (100), 79 (35).

N-5-salicylmaleamic acid (12).

Dark yellow needles from Methanol/H$_2$O, mp=224°–226° C., 46%. $^1$H NMR (DMSO-$d_6$)d 9.8 (s, 1H, NH), 8.2 (d, 1H, C-6 ArH), 7.7 (dd, 1H, C-4 ArH), 6.99 (d, 1H, C-3 ArH), 6.4 (d, 1H, olefinic H), 6.3 (d, 1H, olefinic H). FABMS MH+252 (100), 234 (30), 133 (90), 94 (70).

N-Octylmaleamic acid (15).

White solid. mp=84°–86° C., 81%. $^1$H NMR (DMSO-$d_6$) d 9.3 (t, 1H, NH), 6.4 (d, 1H, olefinic H), 6.2 (d, 1H, olefinic H), 3.2 (q, 2H, -NCH$_2$), 1.1–1.5 (m, 10H, octyl CH$_2$), 0.9 (t, 3H, Terminal-CH$_3$).

N-Nonylmaleamic acid (16).

White crystalline solid, mp=74°–76° C., 79%. $^1$H NMR (DMSO-$d_6$) d 9.0 (bs, 1H, NH), 6.41 (d, 1H, olefinic H), 6.22 (d, 1H, olefinic H), 3.15 (q, 2H, NCH$_2$), 1.0–1.4 (complex multiplet, 14H, methylenes), 0.84 (t, 3H, terminal CH$_3$).

N-Decylmaleamic acid (17).

White crystalline solid, mp=81°–82° C., 88%. $^1$H NMR (DMSO-$d_6$) d 9.1 (bs, 1H, NH), 6.39 (d, 1H, olefinic H), 6.22 (d, 1H, olefinic H), 3.15 (q, 2H, NCH$_2$), 1.1–1.4 (complex multiplet, 16H, methylenes), 0.84 (t, 3H, CH$_3$).

N-(6-Carbonyloxy)pentylmaleamic acid (27).

White crystalline solid from isopropanol/water: mp 171°–173° C., 71%. $^1$H NMR (DMSO-$d_6$) d 9.1 (t, 1H, NH), 6.39 (d, 1H, olefinic H, J=12.4 Hz), 6.22 (d, 1H, olefinic H, J=12.4 Hz), 3.18 (q, 2H, NCH$_2$), 2.19 (t, 2H, methylene adjacent to COOH), 1.25–1.46 (complex multiplet, 6H, methylenes). FABMS MH$^+$ 230.

N-(7-Carbonyloxy)hexylmaleamic acid (28).

White crystalline solid from isopropanol/water: mp 171°–173° C., 84%. $^1$H NMR (DMSO-$d_6$) d 9.1 (t, 1H, NH), 6.39 (d, 1H, olefinic H, J=12.4 Hz), 6.22 (d, 1H, olefinic H, J=12.4 Hz), 3.18 (q, 2H, NCH$_2$), 2.19 (t, 2H, methylene adjacent to COOH), 1.25–1.46 (complex multiplet, 8H, methylenes). FABMS MH$^+$ 244.

N-(8-Carbonyloxy)heptylmaleamic acid (29).

White crystalline solid from isopropanol: mp 179°–181° C., 80%. $^1$H NMR (DMSO-$d_6$) d 9.0 (bs, 1H, NH), 6.39 (d, 1H, olefinic H, J=12.4 Hz), 6.22 (d, 1H, olefinic H, J=124 Hz), 3.15 (q, 2H, NCH$_2$), 2.18 (t, 2H, methylene adjacent to COOH), 1.25–1.46 (complex multiplet, 10H, methylenes). FABMS MH$^+$ 258 (4), 249 (20), 239 (18), 158, ( 46), 110 (100).

N-(11-Carbonyloxy)decylmaleamic acid (30).

White crystalline solid from isopropanol/water: mp 159°–161° C., 85%. $^1$H NMR (DMSO-$d_6$) d 9.1 (t, 1H, NH), 6.39 (d, 1H, olefinic H, J=12.4 Hz), 6.22 (d, 1H, olefinic H, J=12.4 Hz), 3.15 (q, 2H, NCH$_2$), 2.18 (t, 2H, methylene adjacent to COOH), 1.25–1.46 (complex multiplet, 16H, methylenes). EIMS M$^+$ 295 (40), 277 (60), 156 (99), 110 (100).

N-(12-Carbonyloxy)undecylmaleamic acid (31).

White crystalline solid from isopropanol water: mp 160°–162° C., 85%. $^1$H NMR (DMSO-$d_6$) d 9.1 (t, 1H, NH), 6.38 (d, 1H, olefinic H, J=12.4 Hz), 6.22 (d, 1H, olefinic H, J=12.4 Hz), 3.15 (q, 2H, NCH$_2$), 2.18 (t, 2H, methylene adjacent to COOH), 1.25–1.46 (complex multiplet, 18H, methylenes).

N-(8-Carbonyloxy)heptylsuccinamic acid (38).

White crystalline solid from isopropanol water: mp 118°–120° C., 77%. $^1$H NMR (DMSO-$d_6$) d 11.98 (s, 1H, COOH), 7.78 (bs, 1H, NH), 3.0 (q, 2H, CH$_2$), 2.45 (t, 2H, CH$_2$), 2.29 (t, 2H, CH$_2$), 2.18 (t, 2H, CH$_2$), 1.25–1.48 (complex multiplet, 10H, methylenes). EIMS M$^+$ 259 (4).

General Procedure for the Synthesis of N-Substitutedmaleimides and Succmimides.

A reaction mixture containing the appropriate maleamic acid (5.23 mmol) in 5 mL of acetic anhydride and sodium acetate (3 mmol) was heated at 90° C. for 2 hours. The reaction was cooled and quenched with water. The aqueous solution was extracted with Et$_2$O (3×40 mL). The combined ether extracts were dried (Na$_2$SO$_4$), filtered and the solvent was evaporated. The residue was chromatographed on silica gel with EtOAc/hexane. The fractions containing the pure product were combined and concentrated to afford essentially pure maleimide. The product was further recrystallized from isopropanol/water. In the case of the aspirin analogs 13 and 14 purification on silica gel was not needed as the compounds were crystallized from CHC/$_3$/hexane.

N-(o-Methylbenzyl)maleimide (9).

White solid. mp 80°–81.3° C., 51%. $^1$H NMR (DMSO-$d_6$) d 7.3–7.4 (m, 4H, ArH), 6.7 (s, 2H, olefinic H), 4.7 (s, 2H, C$_6$H$_5$CH2), 2.4 (s, 3H, ARCH$_3$). GCMS analysis (Temperature program: 75° C. for 1 min followed by a temperature ramp of 25° C./min for 10 min showed a single peak corresponding to the molecular ion M$^+$ 201.

N-(4-Carbonyloxybenzyl)maleimide (10).

White solid. mp=189°–190° C., 48%. $^1$H NMR (DMSO-d$^6$) d 10.6 (bs, 1H COOH), 7.9 (d, 2H, ArH), 7.4 (d, 2H, ArH), 7.2 (s, 2H, olefinic H), 4.8 (s, 2H, benzylic CH$_2$). FABMS MH$^+$ 234 (25), 216 (30), 133 (100).

N-4-(Maleimido)-2-acetyl-1-benzoic acid (13).

Pale yellow crystals from CH$_2$Cl$_2$/hexane, 61%. $^1$H NMR (CDCl$_3$) d 8.1 (d, 1H, C-6 ArH), 7.4 (dd, 1H, C-5 ArH), 7.3 (d, 1H, C-3 ArH), 6.7 (s, 2H, olefinic H), 2.2 (s, 3H, CH$_3$. EIMS M-18 233 (10), 215 (25), 153 (75), 135, (100), 79 ( 35). FABMS MH$^+$ 276 (20), 258 (35), 216 (100), 158, (95), 134 (85), 118 (80).

N-5-(Maleimido)-2-acetyl-1-benzoic acid (14).

Yellow powder from $CH_2Cl_2$/hexane, mp=190°–192° C., 59%. $^1H$ NMR ($CDCl_3$) d 8.0 (d, 1H, C-6 ArH), 7.7 (dd, 1H, C-5 ArH), 7.3 (d, 1H, C-3 ArH), 6.7 (s, 2H, olefinic H), 2.2 (s, 3H, $CH_3$). FABMS MH+252 (100), 234 (30), 133 (90), 94 (70). FABMS MH$^+$ 276.

N-Octylmaleimide (18).

Off-white semi solid. mp 36°–38° C., 68%. $^1H$ NMR ($CDCl_3$) d 6.6 (s, 2H, olefinic H), 3.3 (t, 2H, $NCH_2$), 1.1–1.5 (m, 10H, octyl $CH_2$), 0.9 (t, 3H, terminal $CH_3$).

N-Nonylmaleimide (19).

White solid from isopropanol/water. (mp 45°–47° C., 49%. $^1H$ NMR ($CDCl_3$) d 6.7 (s, 2H, olefinic H), 3.6 (t, 2H, $NCH_2$), 1.1–1.5 (m, 14H, nonyl $CH_2$), 0.9 (t, 3H, terminal $CH_3$).

N-Decylmaleimide (20).

Off-white solid from isopropanol/water. mp 48°–49° C., 51%. $^1H$ NMR ($CDCl_3$) d 6.7 (s, 2H, olefinic H), 3.6 (t, 2H, $NCH_2$), 1.1–1.5 (m, 16H, decyl $CH_2$), 0.9 (t, 3H, terminal $CH_3$).

N-6-(Maleimido)hexanoic acid (32).

White crystalline solid from 2-propanol/water 49%. $^1H$ NMR (DMSO-$d_6$) d 6.67 (s, 2H, olefinic H), 3.5 (t, 2H, $NCH_2$), 2.3 (t, 2H, methylene adjacent to COOH), 1.4–1.8 (complex multiplet, 6H, methylenes).

N-7-(Maleimido)heptanoic acid (33).

White crystalline solid: mp 91°–92° C., 50%. $^1H$ NMR (DMSO-$d_6$) d 6.67 (s, 2H, olefinic H), 3.5 (t, 2H, $NCH_2$), 2.3 (t, 2H, methylene adjacent to COOH), 1.4–1.8 (complex multiplet, 8H, methylenes).

N-8-(Maleimido)octanoic acid (34).

White crystalline solid from 2-propanol/water: mp 79°–80° C., 80%. $^1H$ NMR (DMSO-$d_6$) d 6.85 (s, 2H, olefinic H), 3.69 (t, 2H, $NCH_2$), 2.6 (t, 2H, methylene adjacent to COOH), 1.4–1.8 (complex multiplet, 10H, methylenes). EIMS M$^+$ 239 (10), 222 (100), 110 (75), 98, (37).

N-11-(Maleimido)undecanoic acid (35).

White crystalline solid from 2-propanol/water: 71%. $^1H$ NMR (DMSO-$d_6$) d 6.85 (s, 2H, olefinic H), 3.5 (t, 2H, $NCH_2$), 2.3 (t, 2H, methylene adjacent to COOH), 1.4–1.8 (complex multiplet, 16H, methylenes). EIMS M$^+$ 281 (25), 263 (35), 110 (100).

N-12-(Maleimido)dodecanoic acid (36).

White crystalline solid from 2-propanol/water: mp 93°–95° C., 75%. $^1H$ NMR (DMSO-$d_6$) d 6.99 (s, 2H, olefinic H), 3.3 (t, 2H, $NCH_2$), 2.18 (t, 2H, methylene adjacent to COOH), 1.4–1.8 (complex multiplet, 18H, methylenes). EIMS M$^+$ 295 (25), 277 (35), 110 (100).

N-8-(Succinimido)octanoic acid (39).

White crystalline solid from 2-propanol/$H_2O$: mp 64°–66° C., 51%. $^1H$ NMR ($CDCl_3$) d 3.6 (t, 2H, $NCH_2$), 2.7 (s, 4H, ring $CH_2$), 2.35 (t, 2H, HOOC-$CH_2$), 1.3– 1.7 (complex multiplet, 10H, methylenes). FABMS MH$^+$ 242 (37), 224 (100), 133 (99), 100 ( 92).

Sebacic Acid Chloride Monomethyl Ester (22).

A reaction mixture containing sebacic acid monomethyl ester (21, 0.5 g, 2.31 mmol) and thionyl chloride (0.55 g, 4.62 mmol) was warmed to 50° C. and allowed to stir at that temperature for 3 h. The excess thionyl chloride was removed under reduced pressure to afford essentially pure 22 as a colorless oil (0.54 g, 100%). $^1H$ NMR ($CDCl_3$) d 3.64 (s, 3H, $OCH_3$), 2.84 (t, 2H, $CH_2$ adjacent to COCl), 2.28 (t, 2H, $CH_2$ adjacent to $COOCH_3$), 1.28– 1.7 (complex multiplet, 12H, methylenes).

Isocyanate (23).

To a solution of the above acid chloride (22, 0.54 g, 2.31 mmol) in 10 mL of dry xylene was added sodium azide (0.15 g, 2.34 mmol) and this reaction mixture was heated under reflux for 2 h. The insoluble residue was filtered off and the solvent was removed under reduced pressure to afford essentially pure 23 as a semisolid material (0.47 g, 97%). $^1H$ NMR ($CDCl_3$) d 3.54 (s, 3H, $OCH_3$), 3.26 (t, 2H, $CH_2$ adjacent to NCO), 2.3 (t, 2H, $CH_2$ adjacent to $COOCH_3$), 1.28–1.7 (complex multiplet, 12H, methylenes).

Hydrochloride Salt of 9-Amino-1-nonanoic acid (24-HCl)

A reaction mixture containing 9-isocyano-1-methyl-nonanoate (23, 0.47 g, 2.2 mmol) in 4 mL of conc HCl was heated under reflux for 2.5 h. The reaction mixture was cooled and the solvent was removed under reduced pressure to afford the crude hydrochloride salt of 24 which was purified by recrystallization from MeOH/$Et_2O$ to afford the desired product as a white crystalline solid in 64% yield. mp 133°–134° C. $^1H$ NMR (DMSO-$d_6$) d 2.74 (t, 2H, $CH_2$ adjacent to $NH_2$), 2.15 (t, 2H, $CH_2$ adjacent to COOH), 1.2–1.52 (complex multiplet, 12H, methylenes).

Maleamic acid (25).

An aqueous solution of the hydrochloride salt of 9-amino-1-nonanoic acid (24•HCl, 0.3 g, 1.73 mmol) was treated with aqueous potassium carbonate till a pH of 7 was obtained. The aqueous solution was evaporated under vacuo and the resultant white solid was stirred with maleic anhydride (4, 0.17 g, 1.73 mmol) in 10 mL of glacial acetic acid overnight. The resultant crystalline white solid which had seperated out of the reaction mixture was filtered and dried. The crude product was recrystallized from isopropanol/water to afford a white crystalline solid 0.4 g, 85%. mp 165°–167° C. $^1H$ NMR (DMSO-$d_6$) d 9.09 (t, 1H, NH), 6.36–6.43 d, 2H, olefinic H), 6.19–6.25 (d, 2H, olefinic H), 3.1–3.2 (q, 2H, $CH_2$ adjacent to CONH), 2.1–2.2 (t, 2H, $CH_2$ adjacent to COOH), 1.24–1.46 (complex multiplet, 12H, methylenes).

9-(Maleimido)-1-nonanoic acid (26).

A reaction mixture containing maleamic acid 25 (0.7 g, 2.58 mmol) in 3 mL of acetic anhydride and sodium acetate (0.12 g, 1.46 mmol) was heated at 90° C. for 2 hours. The reaction was cooled and diluted with water. The aqueous solution was extracted with $Et_2O$ (3×40 mL). The combined ether extracts were dried ($Na_2SO_4$), filtered and the solvent was evaporated. The residue was chromatographed on silica gel with EtOAc/hexane. The fractions containing the pure product were combined and concentrated to afford essentially pure maleimide which was further recrystallized from isopropanol/water to afford the desired product as a white crystalline solid in 52% yield. $^1H$ NMR ($CDCl_3$) d 6.67(s, 2H, olefinic H), 3.46–3.51 (t, 3H,$CH_2$), 2.34 (t, 2H, $CH_2$ adjacent to COOH), 1.24–1.6 (complex multiplet, 12H, methylenes).

EXAMPLE 3

Study of the Enzymology of Synthesized Maleimide Derivatives

The usefulness of the compounds of the present invention as inhibitors of the cyclooxygenase and peroxidase activities of the PGHS enzyme or in treating related diseases or conditions may be demonstrated by their effectiveness in various standard test procedures. A description of the test procedures follows.

Purification of PGHS.

PGHS was purified from ram seminal vesicles.

Assay of Cyclooxygenase Activity.

Oxygen consumption was measured at 37° C. with a Gilson model 5/6 oxygraph equipped with a clark electrode and a thermostatted cuvette. Enzyme aliquots were added to 100 mM Tris-HCl at pH 8 containing 500 µM phenol and 1 mM hematin. Oxygen uptake was initiated by the addition of 100 mM sodium arachidonate, and the initial reaction velocity was determined from the linear portion of the oxygen uptake curve.

Assay of Peroxidase Activity.

Assays were performed on a Shimadzu UV 160U by measuring the initial rates of oxidation of guaiacol at a fixed wavelength (436 nm, kinetic mode) for 20 sec at the rate of 1 sec. Enzyme aliquots were added to 100 mM Tris HCl (pH 8) containing 1 mM heme, 500 µM guaiacol in disposible cuvettes. Reaction was initiated by the addition of 400 µM $H_2O_2$.

Time-Dependent Cyclooxygenase Inhibition Studies with the Maleimide Analogs.

A reaction mixture containing a 100 fold excess of the inhibitor(versus the enzyme concentration) (from a 10 mM stock in DMSO) and holo PGHS (5.3 mg/mL) (reconstituted with one equivalent of hematin) was incubated in a eppendorf tube at room temperature. Aliquots of the incubation mixture, at time intervals of t=0, 30 and 60 min were added to the oxygraph cell already containing 1.25 mL Tris HCL, 100 mM, pH 8, at 37° C., 500 µM phenol and 25 µL of 50 µM hematin. The cyclooxygenase reaction was initiated by the addition of 13 µL of 10 mM sodiumarachidonate in 10% MeOH (final concentration of AA was 100 µM). The oxygen consumption was measured from the linear portion of the $O_2$ uptake curve. In all of the above experiments the final inhibitor concentration in the reaction mixture was 16 µM and that of the enzyme was 0.16 µM. (Table 3)

$IC_{50}$ Measurements for Instantaneous Inactivation of Cyclooxygenase by the N-(Maleimido)alkanoic acid Analogs.

Holo PGHS (250 nM) was placed in the oxygraph cell containing 100 mM Tris-HCl at pH 8 with 500 µM of phenol and 1 µM hematin. The reaction mixture was allowed to reconstitute for 1 min and then varying inhibitor concentration were added to the reaction mixture. As quickly as possible, the cyclooxygenase reaction was initiated by the addition of 100 mM sodium arachidonate. (Table 2)

$IC_{50}$ Measurements for Instantaneous Inactivation of Cyclooxygenase by the N-Substitutedmaleimide Analogs.

Varying inhibitor concentrations were incubated with reconstituted holo PGHS (final concentration in the oxygraph cell was 250 nM) at room temperature for 30 min. Aliquots of this incubation mixture were added to the oxygraph cell containing 100 mM Tris-HCl at pH 8 with 500 µm of phenol and 1 µM hematin. The reaction mixture was allowed to reconstitute for 1 min and the cyclooxygenase reaction was initiated by the addition of 100 mM sodium arachidonate. (Table 1)

Time-Dependent Peroxidase Inhibition Studies with the Maleimide Analogs.

A reaction mixture containing a 100 fold excess of the inhibitor (from a 10 mM stock solution of the inhibitor in DMSO) and holo PGHS (5.3 mg/mL) (reconstituted with one equivalent of hematin) was incubated in a eppendorf tube at room temperature. Aliquots of the incubation mixture (final concentration of the enzyme in the cuvette was 0.25 µM and that of the inhibitor was 21 µM), at time intervals of t=0, 30 and 60 min were added to the UV cuvette containing 100 mM Tris HCL, pH 8, at 37° C., 1 µM hematin and 500 µM guaiacol. The peroxidase reaction was initiated by the addition of 400 µM $H_2O_2$. and the initial rates of oxidation were measured for 20 sec at the repeat rate of 1 sec. (Table 5)

$IC_{50}$ Measurements for Instantaneous Inactivation of Peroxidase by the N-(maleimido)alkanoic Acid Analogs.

A disposible UV cuvette containing 100 mM Tris-HCl (pH 8) and 1 µM hematin and holo PGHS (250 nM) was allowed to equilibrate for 1 min, followed by addition of 0.5 mM guaiacol. This reaction mixture was treated with a given concentration of the inhibitor and then as quickly as possible the peroxidase reaction was initiated by the addition of 0.4 mM $H_2O_2$. The initial rates of oxidation were measured for 20 sec at a repeat rate of 1 second. (Table 4)

Figure 6:
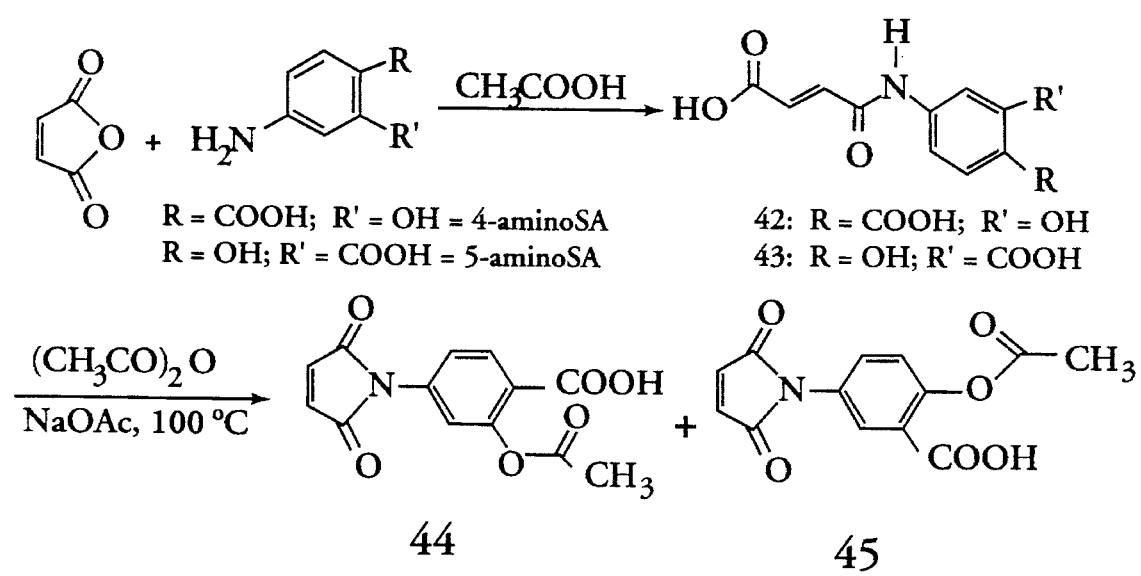
FIG. 6 is a schematic of synthesis of maleimides containing the aspirin moiety. Compound numbers correspond to compound numbers in bold in Example 3.

We have demonstrated the importance of the carboxylic acid functionality present in cyclooxygenase inactivators such as aspirin which is thought to govern (via non-covalent binding) the regioselective acyl transfer to Ser 530. Using a maleimide system substituted with a long alkyl chain containing a terminal COOH group resulted in an efficient inactivator of the cyclooxygenase activity of PGHS. The inhibition was the result of covalent modification of the enzyme as the corresponding saturated succinimide derivative did not inhibit the enzyme, even at a 500 fold excess. The importance of the carboxylic acid group was revealed when removal of this functionality resulted in N-alkylmaleimide analogs which although potent time- and concentration-dependent inactivators of both the cyclooxygenase and peroxidase activity had lost their instantaneous inactivation properties. Inactivation of the enzyme must proceed through an initial non-covalent binding of the maleimides followed by the irreversible inactivation step. The rate of inactivation could be facilitated by the stabilization of the enzyme-inhibitor complex through non-polar interactions. It is quite logical to conclude that prior binding of maleimides facilitated by non-polar interactions (caused with the long alkyl chains) could induce conformational changes that place previously hindered active site nucleophiles such as cysteines in close proximity to the electrophilic center in the maleimides. The ideal chain length between the maleimide ring and the terminal COOH group is 7 methylenes and deviation from this length relatively, results in severe loss of inactivation potency. Despite the failure of the maleimide analog which contained the benzoic acid moiety present in aspirin to efficently inactivate the enzyme, attempts to directly demonstrate the effectiveness of the COOH moiety on aryl tings led to the synthesis of two new aspirin analogs 44 and 45. (FIG. 6)

The selectivity of inhibition demonstrated by these two aspirin analogs $IC_{50}$>200 mM (for compound 44) and 29 mM (for compound 45) is interesting as subtle changes in the substitution pattern in the aspirin moiety led to dramatic effects in terms of inhibition and future prospects include further modification of 45 towards designing better inhibitors. Although at this time it cannot be concluded whether the inhibition was caused by the michael acceptor present in the maleimide ring or by the acetylation of Ser 530 and/or a combination of the two.

One of the attractive prospects of this investigation involves application of the potent and de novo maleimidoalkanoic acids as templates in the rational designing of COX inhibitors. One of the main advantages of these analogs particularly, the N-8-(maleimido)octanoic acid is the low $IC_{50}$ value which could enable administration of relatively small doses for future in vivo studies, such that toxicity would not play a major role.

TABLE 1

Instantaneous Inactivation of the Cyclooxygenase Activity of Holo Prostaglandin Endoperoxide Synthase by Maleimides.

| Compound | IC50 (µM) |
| --- | --- |
| (1) | >800 |
| (2) | 570 |
| (3) | 0.1 |
| (4) | 26 |
| (5) | 37 |
| (6) | 40 |
| (7) | 140 |

In all experiments the enzyme concentrations was 0.25 µM. Approximately 30 different test compounds have been synthesized and screened. Data are presented for a representative set of compounds. Experiments have been performed with all compounds using prostaglandin endoperoxide synthase purified from ram seminal vesicles. At this stage, no experiments have been performed with intact cells or live animals. IC50 represents the concentration of inhibitor required to bring about inhibition of 50% of the cyclooxygenase activity as measured by oxygen consumption.

TABLE 2

IC50 Values for Inactivation of Cyclooxygenase Activity of PGHS

| Compound | IC50 (µM) |
| --- | --- |
| (6) | 29 |
| (7) | >200a |
| (8) | 250 |
| (9) | 50 |
| (10) | 27 |
| (11) | 9 |
| (12) | 12 |
| (13) | 40 |

In all experiments the enzyme concentrations was 0.25 µM. None of the maleimides displayed instantaneous inactivation of the cyclooxygenase activity even at concentrations of 2 mM.

a No significant inhibition observed at 200 µM. The IC50 values were determined from the remaining enzyme activity measured after 30 min of incubation (varying cone of inhibitor) with the enzyme.

In the case of compound 3, the corresponding succinimide was also studied and did not display any inactivation at analogous concentrations and at higher concentrations indicating addition indeed was taking place at the α,β-unsaturated carbonyl moiety.

TABLE 3

Time Dependent Inactivation of Cyclooxygenase Activity by N-Maleimido-omega-aminoacids.

| Inhibitor (µM) | Oxygen Consumption (µM/min) | | |
| --- | --- | --- | --- |
| | T = 0 | T = 30 | T = 60 |
| Control | 221 | 210 | 211 |
| Compound 1, (16 µM) | 212 | 205 | 204 |
| Compound 2, (16 µM) | 195 | 142 | 106 |
| Compound 3, (0.1 µM) | | —a | |
| Compound 4, (10 µM) | 203 | 121 | 68 |
| Compound 5, (10 µM) | 207 | 178 | 81 |
| Compound 6, (9.6 µM) | 170 | 48 | —b |
| Compound 7, (16 µM) | 180 | 27 | —b | a No Time Dependent Inhibition was observed.
b Complete Inhibition observed at the end of min period. Enzyme concentration used was 0.25 µM.

TABLE 4

Studies towards Instantaneous Inactivation of Peroxidase Activity by N-Maleimido-w-aminoacids.

| Compound | IC50 (µM) |
| --- | --- |
| 1 | >800 |
| 2 | >800 (at this conc. 81% activity remains). |
| 3 | 3a |
| 4 | |
| 5 | |
| 6 | >100 |
| 7 | >400 (at this conc. 83% activity remains). | a In the Cyclooxygenase assay this concentration resulted in complete inactivation of enzyme activity. Enzyme concentration was 0.25 µM.

TABLE 5

Time Dependent Inhibition of Peroxidase Activity by Compound 6.
Since except the N-8-(Maleimido)octanoic acid, none of the other maleimidoalkanoic acids revealed instantaneous inactivation at concentrations which resulted in 50% or greater inactivation of cyclooxygenase activity, time dependent inactivation was carried out as a representative case with compound 6.

| Inhibitor (µM) | Change in O.D./min | | |
| --- | --- | --- | --- |
| | T = 0 | T = 30 | T = 60 |
| Control | 1.0387 | 1.0756 | 0.9639 |
| Compound 6, (9.6 µM) | 1.0538 | 0.2408 | 0.1169 |

Enzyme concentration was 0.25 µM. Guaiacol peroxidase substrate assay was employed and initial rate measurements were every 1 second for 20 seconds at a wavelength of 436 nm.

ABBREVIATIONS

| | |
| --- | --- |
| NSAID | Nonsteroidal anti-inflammatory drug |
| PGH | Prostaglandin endoperoxide |
| PGHS | Prostaglandin endoperoxide synthase |
| PGHS-1 | Prostaglandin endoperoxide synthase-I |
| PGHS-2 | Prostaglandin endoperoxide synthase-2 |
| Ser | Serine |
| PG | Prostaglandin |
| LK | Leukotriene |
| PAF | Platelet- Activating Factor |
| DACM | 7-Dimethylamino-4-methyl-coumarinyl) maleimide |
| NEM | N-ethylmaleimide |
| Cys | Cysteine |
| AA | Arachidonic Acid |
| $IC_{50}$ | Concentration at which 50% of the enzyme |

-continued

ABBREVIATIONS

| | |
|---|---|
| | present is inhibited |
| s | Singlet |
| bs | Broad Singlet |
| d | Doublet |
| dd | Doublet of Doublets |
| t | Triplet |
| q | Quartet |
| m | Multiplet |
| EI-MS | Electron Impact Mass Spectra |
| FAB-MS | Fast Atom Bombardment Mass Spectra |
| NaOAc | Sodium Acetate |
| gl. $CH_3COOH$ | Glacial Acetic Acid |
| $(CH_3CO)_2O$ | Acetic Anhydride |
| $NaN_3$ | Sodium Azide |
| $H_2SO_4$ | Sulfuric Acid |
| $K_2CO_3$ | Potassium Carbonate |
| $SOCl_2$ | Thionyl Chloride |
| SA | Salicylic Acid |
| CO | Cyclooxygenase |
| $NA_2SO_4$ | Sodium Sulfate |
| DMSO | Dimethyl Sulfoxide |
| $Et_2O$ | Ether |
| NaOH | Sodium Hydroxide |
| ArH | Benzene |
| $MgSO_4$ | Magnesium Sulfate |
| $CDCl_3$ | Deutereated Chloroform |
| $ArCH_3$ | Methyl Benzene |
| MeOH | Methanol |
| $CH_2Cl_2$ | Methylene Chloride |
| $O_2$ | Molecular Oxygen |

The following references are included to provide details of scientific technology herein incorporated by reference to the extent that they provide additional information for the purposes of indicating the background of the invention or illustrating the state of the art.

REFERENCES

Deitz, K. R.; Nastainczk, W.; and Ruf, H. H. *Eur. J. Biochem.* 1988, 171, 313–320.

DeWitt, D. L.; El-Harith, E. A.; Kraemer, S. A.; Andrews, M. J.; Yao, E. F.; Armstrong, R. L.; and Smith, W. L. (1990) *J. Biol. Chem.* 265, 5192–5198.

Higgs, G. A.; Salmon, J. A.; Henderson, B.; and Vane, J. R. "Pharmacokinetics of aspirin and salicylate in relation to inhibition arachidonate cyclooxygenase and antiinflammatory activity" *Proc. Natl. Acad. Sci.* USA 1986, Vol. 84, 1417–1420.

Humber, L. G. (1987) "Etodolac: The Chemistry, Pharmacology, Metabolic Disposition, and Clinical Profile of a Novel Anti-Inflammatory Pyranocarboxylic Acid" *Medicinal Research Reviews*, Vol. 7, No. 1, 1–28.

Karlen, B.; Lindeke, B.; Lindgren, S.; Svensson, K.-G., Dahlbom, R.; Jenden, D. J.; Giering, J. E. *J. Med. Chem.* 1970, 13, 651–657.

Kulmacz, R. I.; Ren, Y.; Tsai, A. L.; and Balmer, G. *Bioch.* 1990, 29, 8760–8771. Machida, M.; Ushijima, N.; Takahashi, T.; Kanoaka, Y. *Chem. Pharm. Bull.* 1977, 25 (6,), 1289–1294.

Meade, E. A.; Smith, W. L.; and DeWitt, D. L. "Differential Inhibition of Prostaglandin Endoperoxide Synthase (Cyclooxygenase) Isozymes by Aspirin and Other Nonsteroidal Anti-inflammatory Drugs" *The Journal of Biological Chemistry*, 1993, Vol. 268, No. 9, Issue of March 25, 6610–6614.

Pal, I.; Odenwaller, R.; Marnett, L. J. "7-Oxabicycloheptyl-prostanoic Acids: Potent, Time-Dependent Cyclooxygenase Inhibitors That Induce a Conformational Change in the Prostaglandin Synthase Protein". *J. Med. Chem.* 1992, 35, 2340–2342.

Robinson, H. J. and Vane, J. R. "Prostaglandin synthetase Inhibitors- Their Effects on Physiological Functions and Pathological States, Raven, New York." 1990

Rome, L. H. and Lands, W. E. M. "Structural requirements for time-dependent inhibition of prostaglandin biosynthesis by anti-inflammatory drugs" *Proc. Natl. Acad. Sci,* USA, 1975, Vol. 72, No. 12, 4863–4865.

Schoneich, C.; Dillinger U.; Bruchhausen, F.; and Asmus, K. "Oxidation of Polyunsaturated Fatty Acids and Lipids through Thiyl and Sulfonyl Radicals: Reaction Kinetics, and Influence of Oxygen and Structure of Thiyl Radicals" *Archives of Biochemistry and Biophysics,* 1992, Vol. 292, No. 2, 456–467.

Smith, W. L.; DeWitt, D. L.; Shimokawa, T.; Kraemer, S. A.; and Meade, E. A. "Molecular Basis for Inhibition of Prostanoid Biosynthesis by Nonsteroidal Anti-inflammatory Agents", 1990, Vol. 21, No. 12, IV 24-IV 28.

Smith, W. L.; Marnett, L. J. "Prostaglandin Endoperoxide Synthase: Structure and Catalysis." *Biochimica et Biophysica Acta,* 1991, 1083, 1–17.

Vane, J. R. (1971). *Nature* [New Biol.] 231:232–235.

Vane, J. R. and Botting, R. (1987) *FASEB J.* 1: 89–96.

Walsh, D. A.; Young, S.; Shamblee, D. A.; Welstead, W., Jr.; Nolan, J. C.; and Graff, G. "Nonsteroidal Antiinflammatory Drug Hydroxamic Acids. Dual Inhibitors of Both Cyclooxygenase and 5-Lipoxygenase" *J. Med. Chem.,* 1990, 33, 2070–2072.

Wells, I.; and Marnett, L. J. "Acetylation of Prostaglandin Endoperoxide Synthase by N-Acetylimidazole: Comparison to Acetylation by Aspirin" *Biochemistry,* 1992, Vol. 31, No. 40, 520–9525.

Wells, I.; Marnett, L. J. "Inactivation of Prostaglandin Synthase by Acylating Derivatives of Indomethacin" *Biochemistry,* 1993, 32, 2710–2716.

Thus, although there have been described particular embodiments of the present invention of a new and useful nonsteroidal antiinflammatory drug, it is not intended that such references be construed as limitations upon the scope of this invention except as set forth in the following claims. Further, although there have been described certain examples used in the preferred embodiment, it is not intended that such examples be construed as limitations upon the scope of this invention except as set forth in the following claims.

What we claim is:

1. A compound of the formula (II)

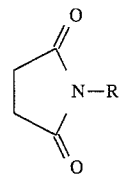

individual isomers thereof, or a pharmaceutically acceptable salt or hydrate thereof wherein R is a moiety selected from the group consisting of an alkyl of 6–11 carbon atoms when substituted by carboxyl, alkyl and carboxyl, phenoxy, or carboxyl substituted phenoxy; phenyl; phenyl when substituted by alkyl, carbonyloxy, or carboxyl and acetyl; benzyl; and benzyl when substituted by alkyl, carboxyl, or carbonyloxy.

2. The compound as in claim 1 which is N-8-(Succinimido)octanoic acid.

3. A compound, individual isomers thereof, or pharmaceutically acceptable salt or hydrate thereof, which is 2-[2-(N-maleimidoethoxy)]benzoic acid.

4. A compound, individual isomers thereof, or pharmaceutically acceptable salt or hydrate thereof, which is N-(4-carbonyloxybenzyl)maleimide.

5. A compound, individual isomers thereof, or pharmaceutically acceptable salt or hydrate thereof, which is N-4-(maleimido)-2-acetyl-1-benzoic acid.

6. A compound, individual isomers thereof, or pharmaceutically acceptable salt or hydrate thereof, which is N-5-(maleimido)-2-acetyl-1-benzoic acid.

7. A compound, individual isomers there of, or pharmaceutically acceptable salt or hydrate thereof, which is 2-[2-(N-maleimidoethoxy)]benzoic acid.

8. A pharmaceutical composition comprising a compound of the formula (I)

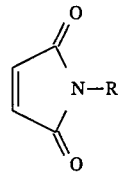

wherein R is a moiety selected from the group consisting of an alkyl of 6–10 carbon atoms; an alkyl of 6–10 carbon atoms when substituted by alkyl, carboxyl, alkyl and carboxyl, phenoxy, or carboxyl substituted phenoxy; phenyl when substituted by alkyl carbonyloxy, or carboxyl and acetyl; and benzyl when substituted by alkyl or carbonyloxy and a pharmaceutical carrier.

9. A pharmaceutical composition comprising a compound of the formula (II)

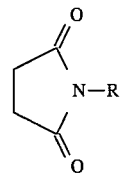

wherein R is a moiety selected from the group consisting of an alkyl of 1–11 carbon atoms when substituted by carboxyl, alkyl and carboxyl, phenoxy, or carboxyl substituted phenoxy; phenyl; phenyl when substituted by alkyl, carbonyloxy, or carboxyl and acetyl; benzyl; and benzyl when substituted by alkyl, carboxyl, or carbonyloxy and a pharmaceutical carrier.

10. The composition described in claim 8 wherein said compound is N-8-(Maleimido)octanoic acid.

11. A pharmaceutical composition comprising an effective amount of a compound having both anti-inflammatory and anti-thrombotic activity, the compound having the formula (I)

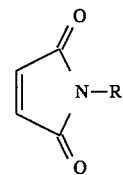

wherein R is a moiety selected from the group consisting of an alkyl of 6–10 carbon atoms when substituted by alkyl, carboxyl, alkyl and carboxyl, phenoxy, or carboxyl substituted phenoxy; phenyl when substituted by alkyl, carbonyloxy, or carboxyl and acetyl; benzyl when substituted by alkyl or carbonyloxy; the pharmaceutically acceptable salts thereof; and an inert carrier.

12. A method of treating inflammation comprising administering to a patient in need thereof a therapeutically effective amount of at least one anti-inflammatory compound, specific for inflammatory pathways, selected from the group consisting of the compound of the formula (I)

individual isomers thereof, or a pharmaceutically acceptable salt or hydrate thereof wherein R is a moiety selected from the group consisting of an alkyl of 1–11 carbon atoms; an alkyl of 1–11 carbon atoms when substituted by alkyl, carboxyl, alkyl and carboxyl, phenoxy, or carboxyl substituted phenoxy; phenyl; phenyl when substituted by alkyl, carbonyloxy, or carboxyl and acetyl; benzyl; and benzyl when substituted by alkyl, carboxyl, or carbonyloxy and the compound of the formula (II)

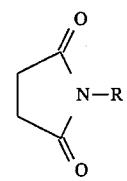

individual isomers thereof, or a pharmaceutically acceptable salt of hydrate thereof wherein R is a moiety selected from the group consisting of an alkyl of 1–11 carbon atoms; an alkyl of 1–11 carbon atoms when substituted by alkyl, carboxyl, alkyl and carboxyl, phenoxy, or carboxyl substituted phenoxy; phenyl; phenyl when substituted by alkyl, carbonyloxy, or carboxyl and acetyl; benzyl; and benzyl when substituted by alkyl, carboxyl, or carbonyloxy.

13. The method described in claim 12 wherein said anti-inflammatory compound is N-(o-Methylbenzyl)maleimide.

14. The method described in claim 12 wherein said anti-inflammatory compound is N-Octylmaleimide.

15. The method described in claim 12 wherein said anti-inflammatory compound is N-Nonylmaleimide.

16. The method described in claim 12 wherein said anti-inflammatory compound is N-Decylmaleimide.

17. The method described in claim 12 wherein said anti-inflammatory compound is N-6-(Maleimido)hexanoic acid.

18. The method described in claim 12 wherein said anti-inflammatory compound is N-7-(Maleimido)heptanoic acid.

19. The method described in claim 12 wherein said anti-inflammatory compound is N-8-(Maleimido)octanoic acid.

20. The method described in claim 12 wherein said anti-inflammatory compound is N-11-(Maleimido)undecanoic acid.

21. The method described in claim 12 wherein said anti-inflammatory compound is N-12-(Maleimido)dodecanoic acid.

22. The method described in claim 12 wherein said anti-inflammatory compound is 9-(Maleimido)-1-nonanoic acid.

23. The method described in claim 12 wherein said anti-inflammatory compound is N-8-(Succinimido)octanoic acid.

24. The method described in claim 12 wherein said anti-inflammatory compound is 2-[2-(N-maleimidoethoxy)] benzoic acid.

25. The method described in claim 12 wherein said anti-inflammatory compound is N-(4-carbonyloxybenzyl) maleimide.

26. The method described in claim 12 wherein said anti-inflammatory compound is N-4-(maleimido)-2-acetyl-1-benzoic acid.

27. The method described in claim 12 wherein said anti-inflammatory compound is N-5-(maleimido)-2-acetyl-1-benzoic acid.

28. A method of treating thrombosis comprising administering to a patient in need thereof a therapeutically effective amount of at least one anti-thrombotic compound, specific for thrombotic pathways, selected from the group consisting of the compound of the formula (I)

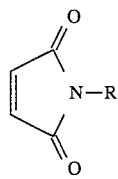

individual isomers thereof, or a pharmaceutically acceptable salt or hydrate thereof wherein R is a moiety selected from the group consisting of an alkyl of 1–11 carbon atoms; an alkyl of 1–11 carbon atoms when substituted by alkyl, carboxyl, alkyl and carboxyl, phenoxy, or carboxyl substituted phenoxy; phenyl; phenyl when substituted by alkyl, carbonyloxy, or carboxyl and acetyl; benzyl; and benzyl when substituted by alkyl, carboxyl, or carbonyloxy and the compound of formula (II)

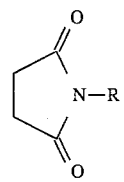

individual isomers thereof, or a pharmaceutically acceptable salt or hydrate thereof wherein R is a moiety selected from the group consisting of an alkyl of 1–11 carbon atoms; an alkyl of 1–11 carbon atoms when substituted by alkyl, carboxyl, alkyl and carboxyl, phenoxy, or carboxyl substituted phenoxy; phenyl; phenyl when substituted by alkyl, carbonyloxy, or carboxyl and acetyl; benzyl; and benzyl when substituted by alkyl; carboxyl, or carbonyloxy.

29. The method described in claim 28 wherein said anti-thrombotic compound is N-(o-Methylbenzyl)maleimide.

30. The method described in claim 28 wherein said anti-thrombotic compound is N-Octylmaleimide.

31. The method described in claim 28 wherein said anti-thrombotic compound is N-Nonylmaleimide.

32. The method described in claim 28 wherein said anti-thrombotic compound is N-Decylmaleimide.

33. The method described in claim 28 wherein said anti-thrombotic compound is N-6-(Maleimido)hexanoic acid.

34. The method described in claim 28 wherein said anti-thrombotic compound is N-7-(Maleimido)heptanoic acid.

35. The method described in claim 28 wherein said anti-thrombotic compound is N-8-(Maleimido)octanoic acid.

36. The method described in claim 28 wherein said anti-thrombotic compound is N-11-(Maleimido)undecanoic acid.

37. The method described in claim 28 wherein said anti-thrombotic compound is N-12-(Maleimido)dodecanoic acid.

38. The method described in claim 28 wherein said anti-thrombotic compound is 9-(Maleimido)-1-nonanoic acid.

39. The method described in claim 28 wherein said anti-thrombotic compound is N-8-(Succinimido)octanoic acid.

40. The method described in claim 28 wherein said anti-thrombotic compound is 2-[2-(N-maleimidoethoxy)] benzoic acid.

41. The method described in claim 28 wherein said anti-thrombotic compound is N-(4-carbonyloxybenzyl)maleimide.

42. The method described in claim 28 wherein said anti-thrombotic compound is N-4-(maleimido)-2-acetyl-1-benzoic acid.

43. The method described in claim 28 wherein said anti-thrombotic compound is N-5-(maleimido)-2-acetyl-1-benzoic acid.

44. A method of inhibiting the cyclooxygenase activity of PGHS comprising the steps of administering to a patient in need thereof a therapeutically affective amount of the compounds of the formula (I)

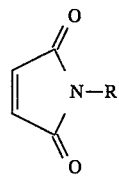

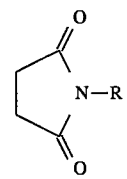

individual isomers thereof, or a pharmaceutically acceptable salt or hydrate thereof wherein R is a moiety selected from the group consisting of an alkyl of 1–11 carbon atoms; an alkyl of 1–11 carbon atoms when substituted by alkyl, carboxyl, alkyl and carboxyl, phenoxy, or carboxyl substituted phenoxy; phenyl; phenyl when substituted by alkyl, carbonyloxy, or carboxyl and acetyl; benzyl; and benzyl when substituted by alkyl, carboxyl, or carbonyloxy and an inert carrier or administering to a patient in need thereof a therapeutically effective amount of the compound (II)

individual isomers thereof, or a pharmaceutically acceptable salt or hydrate thereof wherein R is a moiety selected from the group consisting of an alkyl of 1–11 carbon atoms; an alkyl of 1–11 carbon atoms when substituted by alkyl, carboxyl, alkyl and carboxyl, phenoxy, or carboxyl substituted phenoxy; phenyl; phenyl when substituted by alkyl, carbonyloxy, or carboxyl and acetyl; benzyl; and benzyl when substituted by alkyl, carboxyl, or carbonyloxy and an inert carrier.

\* \* \* \* \*